(12) United States Patent
Nebosky et al.

(10) Patent No.: US 8,475,505 B2
(45) Date of Patent: Jul. 2, 2013

(54) ORTHOPAEDIC SCREWS

(75) Inventors: Paul S. Nebosky, Fort Wayne, IN (US);
Sarah L. Zimmerman, Columbia City, IN (US); Gregory C. Stalcup, Columbia City, IN (US)

(73) Assignee: SMED-TA/TD, LLC, Columbia City, IN (US)

( * ) Notice: Subject to any disclaimer, the term of this patent is extended or adjusted under 35 U.S.C. 154(b) by 386 days.

(21) Appl. No.: 12/540,760

(22) Filed: Aug. 13, 2009

(65) Prior Publication Data
US 2010/0042167 A1    Feb. 18, 2010

Related U.S. Application Data

(60) Provisional application No. 61/088,383, filed on Aug. 13, 2008.

(51) Int. Cl.
*A61B 17/04* (2006.01)

(52) U.S. Cl.
USPC .......................................... 606/304

(58) Field of Classification Search
USPC ............... 606/92–95, 300–321; 411/82, 82.1
See application file for complete search history.

(56) References Cited

U.S. PATENT DOCUMENTS

| | | |
|---|---|---|
| 3,662,405 A | 5/1972 | Bortz et al. |
| 3,683,421 A | 8/1972 | Martinie |
| 3,855,638 A | 12/1974 | Pilliar |
| 3,867,728 A | 2/1975 | Stubstad et al. |
| 4,011,602 A | 3/1977 | Rybicki et al. |
| 4,060,081 A | 11/1977 | Yannas et al. |
| 4,156,943 A | 6/1979 | Collier |
| 4,222,128 A | 9/1980 | Tomonaga et al. |
| 4,450,150 A | 5/1984 | Sidman |
| 4,453,537 A | 6/1984 | Spitzer |
| 4,485,097 A | 11/1984 | Bell |
| 4,520,821 A | 6/1985 | Schmidt et al. |
| 4,608,052 A | 8/1986 | Van Kampen et al. |
| 4,609,551 A | 9/1986 | Caplan et al. |
| 4,620,327 A | 11/1986 | Caplan et al. |
| 4,644,627 A | 2/1987 | Palazzo |

(Continued)

FOREIGN PATENT DOCUMENTS

| | | |
|---|---|---|
| DE | 4211345 C1 | 11/1993 |
| DE | 4423020 A1 | 1/1996 |

(Continued)

OTHER PUBLICATIONS

Office Action dated Jan. 5, 2010 in U.S. Appl. No. 11/060,377 (10 pages).

(Continued)

*Primary Examiner* — Andrew Yang
*Assistant Examiner* — Diana S Jones
(74) *Attorney, Agent, or Firm* — Taylor IP, P.C.

(57) ABSTRACT

An orthopaedic screw having a plurality of regions, at least one of which may be porous. The orthopaedic screw includes a head, a tip and at least one thread. The porosity of the screw of the present invention can vary within the part or region, including changes in pore shape, size and density. These characteristics can vary along the length of the screw axis and/or radially (from the outer diameter to the axis). The orthopaedic screw may further include at least one solid region formed of any implantable polymer, reinforced polymer or metal.

8 Claims, 3 Drawing Sheets

U.S. PATENT DOCUMENTS

| | | | |
|---|---|---|---|
| 4,660,755 A | 4/1987 | Farling et al. |
| 4,737,411 A | 4/1988 | Graves, Jr. et al. |
| 4,769,041 A | 9/1988 | Morscher |
| 4,846,834 A | 7/1989 | Von Recum et al. |
| 4,858,603 A | 8/1989 | Clemow et al. |
| 4,936,859 A | 6/1990 | Morscher et al. |
| 4,976,738 A | 12/1990 | Frey et al. |
| 5,030,233 A | 7/1991 | Ducheyne |
| 5,041,107 A | 8/1991 | Heil, Jr. |
| 5,084,051 A | 1/1992 | Tormala et al. |
| 5,092,898 A | 3/1992 | Bekki et al. |
| 5,100,392 A | 3/1992 | Orth et al. |
| 5,104,410 A | 4/1992 | Chowdhary |
| 5,190,550 A | 3/1993 | Miller et al. |
| 5,197,985 A | 3/1993 | Caplan et al. |
| 5,204,055 A | 4/1993 | Sachs et al. |
| 5,219,363 A | 6/1993 | Crowninshield et al. |
| 5,226,914 A | 7/1993 | Caplan et al. |
| 5,281,210 A | 1/1994 | Burke et al. |
| 5,282,861 A | 2/1994 | Kaplan |
| 5,306,309 A | 4/1994 | Wagner et al. |
| 5,328,765 A | 7/1994 | Anderson et al. |
| 5,370,690 A | 12/1994 | Barrett |
| 5,380,328 A | 1/1995 | Morgan |
| 5,443,471 A | 8/1995 | Swajger |
| 5,458,643 A | 10/1995 | Oka et al. |
| 5,462,362 A | 10/1995 | Yuhta et al. |
| 5,490,962 A | 2/1996 | Cima et al. |
| 5,496,372 A | 3/1996 | Hamamoto et al. |
| 5,514,182 A | 5/1996 | Shea |
| 5,518,680 A | 5/1996 | Cima et al. |
| 5,531,750 A | 7/1996 | Even-Esh |
| 5,537,851 A | 7/1996 | Sheu et al. |
| 5,549,700 A | 8/1996 | Graham et al. |
| 5,571,187 A | 11/1996 | Devanathan |
| 5,593,443 A | 1/1997 | Carter et al. |
| 5,637,175 A | 6/1997 | Feygin et al. |
| 5,641,323 A | 6/1997 | Caldarise |
| 5,702,449 A | 12/1997 | McKay |
| 5,730,817 A | 3/1998 | Feygin et al. |
| 5,732,469 A | 3/1998 | Hamamoto et al. |
| 5,750,103 A | 5/1998 | Cherksey |
| 5,800,828 A | 9/1998 | Dionne et al. |
| 5,807,406 A | 9/1998 | Brauker et al. |
| 5,848,989 A | 12/1998 | Villani |
| 5,849,015 A | 12/1998 | Haywood et al. |
| 5,869,170 A | 2/1999 | Cima et al. |
| 5,871,484 A * | 2/1999 | Spievack et al. ............... 606/60 |
| 5,876,550 A | 3/1999 | Feygin et al. |
| 5,879,406 A | 3/1999 | Lilley |
| 5,916,269 A | 6/1999 | Serbousek et al. |
| 5,971,985 A | 10/1999 | Carchidi et al. |
| 5,989,250 A | 11/1999 | Wagner et al. |
| 6,010,336 A | 1/2000 | Shimotoso et al. |
| 6,045,581 A | 4/2000 | Burkinshaw |
| 6,110,179 A | 8/2000 | Flivik et al. |
| 6,136,029 A | 10/2000 | Johnson et al. |
| 6,139,574 A | 10/2000 | Vacanti et al. |
| 6,143,035 A | 11/2000 | McDowell |
| 6,159,247 A | 12/2000 | Klawitter et al. |
| 6,176,874 B1 | 1/2001 | Vacanti et al. |
| 6,238,435 B1 | 5/2001 | Meulink et al. |
| 6,283,997 B1 | 9/2001 | Garg et al. |
| 6,290,726 B1 | 9/2001 | Pope et al. |
| 6,306,424 B1 | 10/2001 | Vyakarnam et al. |
| 6,315,797 B1 | 11/2001 | Middleton |
| 6,322,564 B1 | 11/2001 | Surma |
| 6,328,765 B1 | 12/2001 | Hardwick et al. |
| 6,333,029 B1 | 12/2001 | Vyakarnam et al. |
| 6,337,198 B1 | 1/2002 | Levene et al. |
| 6,365,149 B2 | 4/2002 | Vyakarnam et al. |
| 6,379,391 B1 | 4/2002 | Masini |
| 6,395,011 B1 | 5/2002 | Johanson et al. |
| 6,409,764 B1 | 6/2002 | White et al. |
| 6,423,095 B1 | 7/2002 | Van Hoeck et al. |
| 6,423,252 B1 | 7/2002 | Chun et al. |
| 6,425,921 B1 | 7/2002 | Grundei et al. |
| 6,440,734 B1 | 8/2002 | Pykett et al. |
| 6,454,811 B1 | 9/2002 | Sherwood et al. |
| 6,461,385 B1 | 10/2002 | Gayer et al. |
| 6,471,689 B1 | 10/2002 | Joseph et al. |
| 6,471,993 B1 | 10/2002 | Shastri et al. |
| 6,475,137 B1 | 11/2002 | Elist |
| 6,494,916 B1 | 12/2002 | Babalola et al. |
| 6,514,514 B1 | 2/2003 | Atkinson et al. |
| 6,526,984 B1 | 3/2003 | Nilsson et al. |
| 6,527,810 B2 | 3/2003 | Johnson et al. |
| 6,530,958 B1 | 3/2003 | Cima et al. |
| 6,533,818 B1 | 3/2003 | Weber et al. |
| 6,534,084 B1 | 3/2003 | Vyakarnam et al. |
| 6,544,472 B1 | 4/2003 | Compton et al. |
| 6,547,824 B1 | 4/2003 | Price |
| 6,551,290 B1 | 4/2003 | Elsberry et al. |
| 6,554,857 B1 | 4/2003 | Zilla et al. |
| 6,565,572 B2 * | 5/2003 | Chappius ..................... 600/300 |
| 6,571,130 B1 | 5/2003 | Ljungstroem et al. |
| 6,599,322 B1 | 7/2003 | Amrich et al. |
| 6,610,095 B1 | 8/2003 | Pope et al. |
| 6,626,950 B2 | 9/2003 | Brown et al. |
| 6,635,049 B1 | 10/2003 | Robinson et al. |
| 6,645,251 B2 | 11/2003 | Salehi et al. |
| 6,656,489 B1 | 12/2003 | Mahmood et al. |
| 6,660,040 B2 | 12/2003 | Chan et al. |
| 6,673,108 B2 | 1/2004 | Zilla et al. |
| 6,682,567 B1 | 1/2004 | Schroeder |
| 6,709,463 B1 | 3/2004 | Pope et al. |
| 6,709,464 B2 | 3/2004 | Scott et al. |
| 6,712,850 B2 | 3/2004 | Vyakarnam et al. |
| 6,723,120 B2 | 4/2004 | Yan |
| 6,783,546 B2 | 8/2004 | Zucherman et al. |
| 6,818,620 B2 | 11/2004 | Bhatnagar |
| 6,852,272 B2 | 2/2005 | Artz et al. |
| 6,863,899 B2 | 3/2005 | Koblish et al. |
| 6,866,685 B2 | 3/2005 | Chan et al. |
| 6,881,413 B1 | 4/2005 | Bartholeyns |
| 6,893,465 B2 | 5/2005 | Huang |
| 6,913,623 B1 | 7/2005 | Zhu |
| 6,916,321 B2 | 7/2005 | TenHuisen et al. |
| 6,969,383 B2 | 11/2005 | Hildebrand |
| 6,989,033 B1 | 1/2006 | Schmidt |
| 6,993,406 B1 | 1/2006 | Cesarano, III et al. |
| 7,018,418 B2 | 3/2006 | Amrich et al. |
| 7,052,710 B2 | 5/2006 | Giordano et al. |
| 7,077,867 B1 | 7/2006 | Pope et al. |
| 7,087,086 B2 | 8/2006 | Li et al. |
| 7,087,200 B2 | 8/2006 | Taboas et al. |
| 7,094,371 B2 | 8/2006 | Lo |
| 7,108,828 B2 | 9/2006 | Lefebvre et al. |
| 7,174,282 B2 | 2/2007 | Hollister et al. |
| 7,189,409 B2 | 3/2007 | Pirhonen et al. |
| 7,192,440 B2 | 3/2007 | Andreas et al. |
| 7,208,222 B2 | 4/2007 | Rolfe et al. |
| 7,226,612 B2 | 6/2007 | Sohier et al. |
| 7,238,363 B2 | 7/2007 | Mansouri et al. |
| 7,250,055 B1 * | 7/2007 | Vanderwalle ................ 606/92 |
| 7,250,060 B2 | 7/2007 | Trieu |
| 7,255,713 B2 | 8/2007 | Malek |
| 7,300,439 B2 | 11/2007 | May |
| 7,537,617 B2 | 5/2009 | Bindsell et al. |
| 7,537,664 B2 | 5/2009 | O'Neill et al. |
| 7,575,572 B2 | 8/2009 | Sweeny |
| 7,632,228 B2 | 12/2009 | Brauker et al. |
| 7,632,338 B2 | 12/2009 | Cipollini |
| 7,666,230 B2 | 2/2010 | Orban et al. |
| 7,674,426 B2 | 3/2010 | Grohowski, Jr. |
| 7,674,477 B1 | 3/2010 | Schmid et al. |
| 7,717,956 B2 | 5/2010 | Lang |
| 2001/0038848 A1 | 11/2001 | Donda et al. |
| 2001/0039455 A1 | 11/2001 | Simon et al. |
| 2002/0022884 A1 | 2/2002 | Mansmann |
| 2002/0029083 A1 | 3/2002 | Zucherman et al. |
| 2002/0035400 A1 | 3/2002 | Bryan et al. |
| 2002/0062154 A1 | 5/2002 | Ayers |
| 2002/0072798 A1 | 6/2002 | Riesle et al. |
| 2002/0106393 A1 | 8/2002 | Bianchi et al. |
| 2002/0128715 A1 | 9/2002 | Bryan et al. |
| 2002/0143402 A1 | 10/2002 | Steinberg |

| Publication No. | Date | Name |
|---|---|---|
| 2002/0161447 A1 | 10/2002 | Salehi et al. |
| 2002/0182241 A1 | 12/2002 | Borenstein et al. |
| 2002/0183850 A1 | 12/2002 | Felt et al. |
| 2002/0197178 A1 | 12/2002 | Yan |
| 2003/0003127 A1 | 1/2003 | Brown et al. |
| 2003/0004578 A1 | 1/2003 | Brown et al. |
| 2003/0006534 A1 | 1/2003 | Taboas et al. |
| 2003/0060891 A1 | 3/2003 | Shah |
| 2003/0069465 A1 | 4/2003 | Benkowski et al. |
| 2003/0097182 A1 | 5/2003 | Buchman et al. |
| 2003/0114934 A1 | 6/2003 | Steinberg |
| 2003/0118649 A1 | 6/2003 | Gao et al. |
| 2003/0130743 A1 | 7/2003 | Scott et al. |
| 2003/0139809 A1 | 7/2003 | Worst et al. |
| 2003/0171738 A1 | 9/2003 | Konieczynski et al. |
| 2003/0171820 A1 | 9/2003 | Wilshaw et al. |
| 2003/0180171 A1 | 9/2003 | Artz et al. |
| 2003/0187513 A1 | 10/2003 | Durniak |
| 2003/0203002 A1 | 10/2003 | Murphy et al. |
| 2003/0206928 A1 | 11/2003 | Tormala et al. |
| 2004/0024470 A1 | 2/2004 | Giordano et al. |
| 2004/0034357 A1 | 2/2004 | Beane et al. |
| 2004/0034427 A1 | 2/2004 | Goel et al. |
| 2004/0063206 A1 | 4/2004 | Rowley et al. |
| 2004/0073197 A1 | 4/2004 | Kim |
| 2004/0115172 A1 | 6/2004 | Bianchi et al. |
| 2004/0126405 A1 | 7/2004 | Sahatjian et al. |
| 2004/0147905 A1 | 7/2004 | Krumme |
| 2004/0153165 A1 | 8/2004 | Li et al. |
| 2004/0180072 A1 | 9/2004 | Tunc et al. |
| 2004/0191106 A1 | 9/2004 | O—Neill et al. |
| 2004/0191292 A1 | 9/2004 | Chou |
| 2004/0193273 A1 | 9/2004 | Huang |
| 2004/0199260 A1 | 10/2004 | Pope et al. |
| 2004/0210274 A1 | 10/2004 | Bauhahn et al. |
| 2004/0210316 A1 | 10/2004 | King et al. |
| 2004/0215173 A1 | 10/2004 | Kunst |
| 2004/0225360 A1 | 11/2004 | Malone |
| 2004/0249463 A1 | 12/2004 | Bindseil et al. |
| 2004/0265350 A1 | 12/2004 | Sambrook et al. |
| 2004/0267263 A1* | 12/2004 | May ................ 606/72 |
| 2005/0015059 A1 | 1/2005 | Sweeney |
| 2005/0021084 A1 | 1/2005 | Lu et al. |
| 2005/0049715 A1 | 3/2005 | Ito et al. |
| 2005/0049716 A1 | 3/2005 | Wagener et al. |
| 2005/0058684 A1 | 3/2005 | Shanley et al. |
| 2005/0059972 A1 | 3/2005 | Biscup |
| 2005/0085888 A1 | 4/2005 | Andreas et al. |
| 2005/0100470 A1 | 5/2005 | Lefebvre et al. |
| 2005/0100578 A1 | 5/2005 | Schmid et al. |
| 2005/0112397 A1 | 5/2005 | Rolfe et al. |
| 2005/0125073 A1 | 6/2005 | Orban et al. |
| 2005/0137707 A1 | 6/2005 | Malek |
| 2005/0175703 A1 | 8/2005 | Hunter et al. |
| 2005/0177238 A1 | 8/2005 | Khandkar et al. |
| 2005/0177247 A1 | 8/2005 | Canham et al. |
| 2005/0182494 A1 | 8/2005 | Schmid |
| 2005/0187555 A1 | 8/2005 | Biedermann et al. |
| 2005/0192669 A1 | 9/2005 | Zdeblick et al. |
| 2005/0197654 A1 | 9/2005 | Edman et al. |
| 2005/0202371 A1 | 9/2005 | McGuire |
| 2005/0220837 A1 | 10/2005 | Disegi et al. |
| 2005/0222688 A1 | 10/2005 | Zilla et al. |
| 2005/0228503 A1 | 10/2005 | Gundolf |
| 2005/0246032 A1 | 11/2005 | Bokros et al. |
| 2005/0271694 A1 | 12/2005 | Mansouri et al. |
| 2005/0272153 A1 | 12/2005 | Xuenong et al. |
| 2005/0273082 A1 | 12/2005 | Olsen |
| 2005/0273178 A1 | 12/2005 | Boyan et al. |
| 2006/0002810 A1 | 1/2006 | Grohowski, Jr. |
| 2006/0015186 A1 | 1/2006 | Isaac |
| 2006/0047341 A1 | 3/2006 | Trieu |
| 2006/0057737 A1 | 3/2006 | Santini, Jr. et al. |
| 2006/0064170 A1 | 3/2006 | Smith et al. |
| 2006/0083730 A1 | 4/2006 | Kusanagi et al. |
| 2006/0093646 A1 | 5/2006 | Cima et al. |
| 2006/0100706 A1 | 5/2006 | Shadduck et al. |
| 2006/0100716 A1 | 5/2006 | Lerf |
| 2006/0105015 A1 | 5/2006 | Perla et al. |
| 2006/0111782 A1 | 5/2006 | Petersen |
| 2006/0111785 A1 | 5/2006 | O'Neil |
| 2006/0121609 A1 | 6/2006 | Yannas et al. |
| 2006/0129242 A1 | 6/2006 | Bergeron et al. |
| 2006/0149220 A1 | 7/2006 | Ullestad et al. |
| 2006/0149386 A1 | 7/2006 | Clarke et al. |
| 2006/0178744 A1 | 8/2006 | de Villiers et al. |
| 2006/0193885 A1 | 8/2006 | Leonard Neethling et al. |
| 2006/0195188 A1 | 8/2006 | O'Driscoll et al. |
| 2006/0204581 A1 | 9/2006 | Gower et al. |
| 2006/0229715 A1 | 10/2006 | Istephanous et al. |
| 2006/0241593 A1* | 10/2006 | Sherman et al. ................ 606/61 |
| 2006/0264950 A1 | 11/2006 | Nelson et al. |
| 2006/0271022 A1 | 11/2006 | Steinbach et al. |
| 2006/0271201 A1 | 11/2006 | Kumar et al. |
| 2006/0282166 A1 | 12/2006 | Molz et al. |
| 2006/0287689 A1 | 12/2006 | Debruyne et al. |
| 2006/0289388 A1 | 12/2006 | Yang et al. |
| 2006/0293757 A1 | 12/2006 | McKay et al. |
| 2007/0016163 A1 | 1/2007 | Santini, Jr. et al. |
| 2007/0026069 A1 | 2/2007 | Shastri et al. |
| 2007/0038299 A1 | 2/2007 | Stone et al. |
| 2007/0041952 A1 | 2/2007 | Guilak et al. |
| 2007/0043446 A1 | 2/2007 | Murray |
| 2007/0077267 A1 | 4/2007 | Molz, IV et al. |
| 2007/0105222 A1 | 5/2007 | Wolfinbarger et al. |
| 2007/0116734 A1 | 5/2007 | Akash |
| 2007/0123843 A1 | 5/2007 | Gill |
| 2007/0138042 A1 | 6/2007 | Wood |
| 2007/0141105 A1 | 6/2007 | Stein et al. |
| 2007/0141533 A1 | 6/2007 | Ford et al. |
| 2007/0150068 A1 | 6/2007 | Dong et al. |
| 2007/0160681 A1 | 7/2007 | Park et al. |
| 2007/0161986 A1 | 7/2007 | Levy |
| 2007/0162110 A1 | 7/2007 | Dave |
| 2007/0166348 A1 | 7/2007 | Van Dyke |
| 2007/0168021 A1 | 7/2007 | Holmes, Jr. et al. |
| 2007/0185585 A1 | 8/2007 | Bracy et al. |
| 2007/0190880 A1 | 8/2007 | Dubrow et al. |
| 2007/0191963 A1 | 8/2007 | Winterbottom et al. |
| 2007/0196419 A1 | 8/2007 | Teller et al. |
| 2007/0202145 A1 | 8/2007 | Ghabrial et al. |
| 2007/0203584 A1 | 8/2007 | Bandyopadhyay et al. |
| 2007/0208420 A1 | 9/2007 | Ameer et al. |
| 2007/0233071 A1 | 10/2007 | Dewey et al. |
| 2007/0243225 A1 | 10/2007 | McKay |
| 2007/0250169 A1 | 10/2007 | Lang |
| 2007/0255262 A1 | 11/2007 | Haase |
| 2007/0270859 A1 | 11/2007 | Companioni et al. |
| 2008/0015578 A1 | 1/2008 | Erickson et al. |
| 2008/0119945 A1 | 5/2008 | Frigg |
| 2009/0024224 A1 | 1/2009 | Chen et al. |
| 2010/0003639 A1 | 1/2010 | Salvi et al. |
| 2010/0042167 A1 | 2/2010 | Nebosky et al. |
| 2010/0042213 A1 | 2/2010 | Nebosky et al. |
| 2010/0042214 A1 | 2/2010 | Nebosky et al. |
| 2010/0042215 A1 | 2/2010 | Stalcup et al. |
| 2010/0042218 A1 | 2/2010 | Nebosky et al. |
| 2010/0042226 A1 | 2/2010 | Nebosky et al. |
| 2010/0190254 A1 | 7/2010 | Chian et al. |
| 2010/0291286 A1 | 11/2010 | O'Neill et al. |
| 2011/0064784 A1 | 3/2011 | Mullens et al. |
| 2011/0153028 A1 | 6/2011 | Albertorio |

FOREIGN PATENT DOCUMENTS

| | | |
|---|---|---|
| DE | 693 28 047 T2 | 3/2000 |
| DE | 19904436 A1 | 8/2000 |
| DE | 10051438 A1 | 5/2002 |
| DE | 695 28 346 T2 | 9/2002 |
| DE | 10120330 A1 | 11/2002 |
| DE | 10157315 C1 | 8/2003 |
| EP | 0617931 A2 | 10/1994 |
| EP | 0827726 A2 | 3/1998 |
| EP | 1 287 851 A1 | 3/2003 |
| EP | 1475057 A1 | 11/2004 |
| EP | 1806112 A1 | 7/2007 |
| FR | 2697155 A1 | 4/1994 |
| JP | 6007388 A | 1/1994 |
| JP | 7116184 A | 5/1995 |

| | | | |
|---|---|---|---|
| JP | 8173463 A | 7/1996 | |
| JP | 2587625 B2 | 12/1996 | |
| JP | 2002325781 A | 11/2002 | |
| JP | 2005329179 A | 12/2005 | |
| WO | 03026714 A1 | 4/2003 | |
| WO | 03084602 A2 | 10/2003 | |
| WO | 03101504 A1 | 12/2003 | |
| WO | 2005/047467 A2 | 5/2005 | |
| WO | 2006/088480 A2 | 8/2006 | |
| WO | 2006/135727 A2 | 12/2006 | |

OTHER PUBLICATIONS

Office Action dated Sep. 24, 2010 in U.S. Appl. No. 11/060,377 (7 pages).
A. Cameron, entitled "Basic Lubrication Theory", Ellis Horwood Limited, pp. 134-137, 1976.
A. Cameron, entitled "The Principles of Lubrication", John Wiley and Sons Inc., pp. 542-559, 1966.
Office Action dated May 12, 2010 in U.S. Appl. No. 10/980,425 (22 pages).
Philip E. Mitchell, Handbook Editor, "Tool and Manufacturing Engineers Handbook", 4th Edition, vol. VIII Plastic Part Manufacturing, Society of Manufacturing Engineers, Dearborn, Michigan, pp. 2-17 and 2-18, 1996 (4 pages).
U.S. Appl. No. 60/149,027, filed Aug. 16, 1999 with U.S. Patent & Trademark Office (44 pages).
U.S. Appl. No. 08/200,636, filed Feb. 23, 1994 with U.S. Patent & Trademark Office (40 pages).
Office Action dated Apr. 17, 1995 in U.S. Appl. No. 08/200,636 (4 pages).
Supplemental Information Disclosure Statement dated Sep. 11, 1995 in U.S. Appl. No. 08/200,636 (7 pages).
U.S. Appl. No. 08/437,781, filed May 9, 1995 with U.S. Patent & Trademark Office (84 pages).
Office Action dated Nov. 1, 1996 in U.S. Appl. No. 08/437,781 (2 pages).
U.S. Appl. No. 09/639,612, filed Aug. 15, 2000 with U.S. Patent & Trademark Office (67 pages).
International Search Report, International Serial No. PCT/US2009/053735, dated Sep. 28, 2009.
International Search Report dated Sep. 28, 2009 of International Searching Authority for Application No. PCT/US2009/053724 (2 pages).
International Search Report dated Sep. 28, 2009 of International Searching Authority for Application No. PCT/US2009/053735 (2 pages).
International Search Report dated Sep. 23, 2009 of International Searching Authority for Application No. PCT/US2009/053762 (2 pages).
International Search Report dated Oct. 14, 2009 of International Searching Authority for Application No. PCT/US2009/053751 (2 pages).
Joseph P. Vacanti, Martin A. Morse, W. Mark Saltzman, Abraham J. Domb, Antonio Perez-Atayde, and Robert Langer; article entitled "Selective Cell Transplantation Using Bioabsorbable Artificial Polymers as Matrices", Journal of Pediatric Surgery, vol. 23, No. 1, pp. 3-9, Jan. 1988, published by Grune & Stratton, Inc.
N.R. Boeree, J. Dove, J.J. Cooper, J. Knowles, and G.W. Hastings, article entitled "Development of a Degradable Composite for Orthopaedic Use: Mechanical Evaluation of an Hydroxyapatite-Polyhydroxybutyrate Composite Material", Biomaterials, vol. 14, No. 10, pp. 793-796, 1993, published by Butterworth-Heinemann Ltd.
R.B. Martin, M.W. Chapman, N.A. Sharkey, S.L. Zissimos, B. Bay, and E.C. Shors, article entitled "Bone Ingrowth and Mechanical Properties of Coralline Hydroxyapatite 1 Yr After Implantation", Biomaterials, vol. 14, No. 5, pp. 341-348, 1993, published by Butterworth-Heinemann Ltd.
Article entitled "Fractal" (nine pages), published on the Internet by the online encyclopedia Wikipedia; downloaded from the internet on Dec. 14, 2006 in the United States from the following address: http://en.wikipedia.org/wiki/Fractals.

Editor in Chief Sybil P. Parker, p. 799 (showing entries from "fp" to "fracture test") of McGraw-Hill Dictionary of Scientific and Technical Terms, Fifth Edition, published by McGraw-Hill, Inc., 1994, New York.
Office Action dated Oct. 31, 2008 in U.S. Appl. No. 10/980,425 (20 pages).
Office Action dated Oct. 20, 2006 in U.S. Appl. No. 11/060,377 (10 pages).
Written Opinion dated Sep. 28, 2009 of International Searching Authority for Application No. PCT/US2009/053724 (8 pages).
Written Opinion dated Sep. 28, 2009 of International Searching Authority for Application No. PCT/US2009/053735 (7 pages).
Written Opinion dated Sep. 23, 2009 of International Searching Authority for Application No. PCT/US2009/053762 (4 pages).
Written Opinion dated Oct. 14, 2009 of International Searching Authority for Application No. PCT/US2009/053751 (6 pages).
Article entitled "Rolled Threads" (3 pages), published on the Internet by the online encyclopedia Wikipedia; downloaded from the internet on Aug. 24, 2009 in the United States from the following address: http://en.wikipedia.org/wiki/File:American_Machinists_Handbook--2e--p23--v001.png.
Written Opinion dated Apr. 13, 2010 of International Searching Authority for Application No. PCT/US2009/055380 (8 pages).
Written Opinion dated Oct. 13, 2009 of International Searching Authority for Application No. PCT/US2009/055397 (9 pages).
Unknown Author, article entitled "MacroPore Resorbable Technology: An Overview", Scientific Data Series in Resorbable Fixation, MKT004 Rev. 6/01, pp. 1-8; distributed by Medtronic Sofamor Danek, 1800 Pyramid Place, Memphis TN 38132, (Jun. 2001).
Ralph E. Holmes, M.D., Stefan M. Lemperle, M.D., and Christopher J. Calhoun, M.B.A., article entitled "Protected Bone Regeneration", Scientific Data Series in Resorbable Fixation, MKT003 Rev. 6/01, pp. 1-10; distributed by Medtronic Sofamor Danek, 1800 Pyramid Place, Memphis TN 38132, (Jun. 2001).
D.R. Sumner, T.M. Turner, R.M. Urban, R.M. Leven, M. Hawkins, E.H. Nichols, J.M. McPherson, J.O. Galante, article entitled "Locally Delivered rhTGF-B2 Enhances Bone Ingrowth and Bone Regeneration at Local and Remote Sites of Skeletal Injury", Journal of Orthopaedic Research 19 (2001) pp. 85-94, published by Elsevier Science Ltd.
International Search Report dated May 18, 2005 of International Searching Authority for Application No. PCT/US2004/036997 (3 pages).
U.S. Appl. No. 08/048,408, filed Apr. 15, 1993 with U.S. Patent & Trademark Office (108 pages).
Preliminary Amendment dated Jul. 8, 1993 and filed in U.S. Appl. No. 08/048,408 with U.S. Patent & Trademark Office (12 pages).
Machine English translation of JP 2587625 (10 pages).
International Preliminary Report on Patentability dated May 8, 2006 of International Searching Authority for Application No. PCT/US2004/036997 (6 pages).
Written Opinion dated May 18, 2005 of International Searching Authority for Application No. PCT/US2004/036997 (5 pages).
Communication and supplementary European search report dated Nov. 14, 2008 from European Patent Office in application No. 04818642 (3 pages).
Office Action dated Jun. 25, 2010 from European Patent Office in application No. 04818642 (5 pages).
International Search Report dated Mar. 12, 2007 of International Searching Authority for PCT/US2005/019045 (3 pages).
International Preliminary Report on Patentability dated Aug. 21, 2007 of International Searching Authority for Application No. PCT/US2005/019045 (7 pages).
Written Opinion dated Mar. 12, 2007 of International Searching Authority for Application No. PCT/US2005/019045 (6 pages).
Office Action dated May 7, 2007 in U.S. Appl. No. 11/060,377 (13 pages).
Office Action dated Aug. 20, 2007 in U.S. Appl. No. 11/060,377 (3 pages).
Office Action dated Feb. 20, 2008 in U.S. Appl. No. 11/060,377 (5 pages).
Office Action dated Sep. 2, 2008 in U.S. Appl. No. 11/060,377 (7 pages).

Office Action dated Dec. 15, 2008 in U.S. Appl. No. 11/060,377 (8 pages).
Interview Summary dated Mar. 5, 2009 in U.S. Appl. No. 11/060,377 (2 pages).
Office Action dated May 27, 2009 in U.S. Appl. No. 11/060,377 (7 pages).
International Preliminary Report on Patentability dated Feb. 15, 2011 for PCT/US2009/053724 (9 pages).
International Preliminary Report on Patentability dated Feb. 15, 2011 for PCT/US2009/053735 (8 pages).
International Preliminary Report on Patentability dated Feb. 15, 2011 for PCT/US2009/053751 (7 pages).
International Preliminary Report on Patentability dated Feb. 15, 2011 for PCT/US2009/053762 (5 pages).
International Preliminary Report on Patentability dated Mar. 1, 2011 for PCT/US2009/055380 (9 pages).
International Preliminary Report on Patentability dated Mar. 1, 2011 for PCT/US2009/055397 (10 pages).
Photos 309 and 310 show a poster of which Applicant is aware. By disclosing these photos, Applicant is making no statement as to whether or not these photos are material or are prior art relative to the present application.
International Search Report dated Apr. 13, 2010 of International Searching Authority for Application No. PCT/US2009/055380 (2 pages).
International Search Report dated Oct. 13, 2009 of International Searching Authority for Application No. PCT/US2009/055397 (2 pages).
Office Action dated Oct. 9, 2007 in U.S. Appl. No. 10/980,425 (16 pages).
Office Action dated Apr. 7, 2008 in U.S. Appl. No. 10/980,425 (20 pages).
Office Action dated Jul. 17, 2008 in U.S. Appl. No. 10/980,425 (3 pages).
Office Action dated Oct. 29, 2008 in U.S. Appl. No. 11/325,530 (11 pages).
Office Action dated Jun. 26, 2009 in U.S. Appl. No. 11/325,530 (13 pages).
Office Action dated Oct. 19, 2009 in U.S. Appl. No. 11/325,530 (6 pages).
Robert J. Klebe; article entitled "Cytoscribing: A Method for Micropositioning Cells and the Construction of Two- and Three-Dimensional Synthetic Tissues", Experimental Cell Research 179 (1988) 362-373, published by Academic Press, Inc.
Emanuel Sachs, Michael Cima, James Bredt, Alain Curodeau, Tailin Fan, and David Brancazio; article entitled "Cad-Casting: Direct Fabrication of Ceramic Shells and Cores by Three Dimensional Printing", Manufacturing Review vol. 5, No. 2, pp. 117-126, Jun. 1992, published by American Society of Mechanical Engineers.

* cited by examiner

ORTHOPAEDIC SCREWS

CROSS REFERENCE TO RELATED APPLICATIONS

This is a non-provisional application based upon U.S. provisional patent application Ser. No. 61/088,383, entitled "ORTHOPAEDIC SCREWS", filed Aug. 13, 2008, which is incorporated herein by reference.

BACKGROUND OF THE INVENTION

1. Field of the Invention

The present invention relates to orthopaedic devices, and, more particularly, to orthopedic screws.

2. Description of the Related Art

A number of solid metal and resorbable polymer (e.g. PLLA, PGA) screws are known. These screws are generally meant to provide short term (9 months or less) attachment of the soft tissue to the bone until healing and integration can occur.

There are a number of problems associated with the known metal and resorbable screws. Due to the density of the metals that are used in the solid metal screws, it is difficult to examine bone or soft tissue that is near the screw via x-ray, CT, or MRI scan. The screw causes a significant 'white-out' in the region of the screw. Tissue healing and integration around the screw is critical to the success of the surgery, thus the ability to evaluate the tissue near the screw is valuable. In addition, the solid metal screws have issues with poor initial fixation and later pull-out of the soft tissue (e.g. pull out of an ACL from the bone) does occur. These are painful and can require follow-up surgery. Certainly any improvements to reduce the rate of pull-out and additional surgery would be desirable.

With respect to the known resorbable screws, issues with poor initial fixation and pull-out also exist. The rate of resorbtion of the polymer can be difficult to control and can occur too quickly for a given patient, increasing the risk of soft tissue pull-out. Further, resorbable materials have been shown to induce fibrous tissue formation between the resorbable implant and the bone, increasing the risk of soft tissue pull-out. This may be due to the local chemistry created as the polymer dissolves.

What is needed in the art is an orthopaedic screw that allows for more effective fixation of the tissue and visualization with known imaging devices of the tissue near and surrounding the screw.

SUMMARY OF THE INVENTION

The present invention provides porous screws and screws that can deliver therapeutic agents. Further, the present invention provides a porous screw for attaching various soft tissues to bone, and/or for attaching bone to bone, and/or for delivering therapeutic agents (for example biologics or drugs) to soft tissue and/or bone. Potential uses include, but are not limited to, ACL and PCL reconstruction, medial collateral ligament repair, lateral collateral ligament repair, posterior oblique ligament repair, iliotibial band tenodesis reconstruction, patellar ligament and tendon repair, pedicle screws for spine repair, bone fracture fixation screw, and drug eluting implant (non-load bearing) for delivery of therapeutics.

One embodiment of the present invention provides an orthopaedic screw having a plurality of regions, at least one of which may be porous. The orthopaedic screw includes a head, a tip and at least one thread. The porosity of the screw of the present invention can vary within the part or region, including changes in pore shape, size and density. These characteristics can vary along the length of the screw axis and/or radially (from the outer diameter to the axis).

The orthopaedic screw of the present invention may further include at least one solid region formed of any implantable polymer, reinforced polymer or metal. The solid region of material may be, for example, at the outer portion of the threads and the leading tip of the screw due to the high stresses present during insertion. The solid region may further include the head of the orthopaedic screw of the present invention.

The materials to create the orthopaedic screw of the present invention can be any implantable polymer, metal or ceramic, or any combination thereof. Possible polymers include polyetheretherketone (PEEK), polyetherketone (PEK), polyaryletherketone (PAEK), polyethylene, and resorbable polymers such as polylactic acid (PLA) and polyglycolic acid (PGA).

The thread of the orthopaedic screw of the present invention may be continuous or discontinuous and be a single or multiple lead thread. The inventive screw may further be cannulated or non-cannulated.

The orthopaedic screw of the present invention may further be used to locally deliver therapeutic agents that promote positive tissue response (e.g. increased growth rate, decreased inflammatory response). Such therapeutic agents include, but are not limited to, hydroxyapatite, drugs and biologics.

A second embodiment of the orthopaedic screw of the present invention provides for immediate delivery of a therapeutic agent through channels and/or holes and reservoirs for long-term delivery of a therapeutic agent. Access to the delivery channels, holes and/or reservoirs may be gained by provision of a self-sealing polymer diaphragm which can allow for direct interface with a needle at the time of surgery of post-surgery. Alternatively, a removable cap made of PEEK or other implantable material may provide access to and seal the medicine delivery features of the inventive screw.

A third embodiment of the inventive orthopaedic screw composed of radiolucent material includes a radiopaque marker to indicate position and orientation of the implant on an x-ray, fluoroscope, or similar diagnostic tool. The markers can be made of any number of more dense implantable materials. Options include, but are not limited to implantable metals (stainless steel, titanium, or titanium alloys for example), barium sulfate filled PEEK, carbon filled PEEK, and other polymers with radiopaque material (such as barium sulfate or zirconium dioxide). Examples of the marker structure include one or more of the following: a pin filling some or all of the cannula of a cannulated screw, one of material layers of the inventive screw if manufactured by layering, all or some of the threads, a cross pin, or the head or tip of the screw. The opacity and/or amount of radiopaque material can be controlled so that the marker does not prevent evaluation of the tissue near the screw by x-ray or other diagnostic methods.

An advantage of the present invention is that the porous nature of the inventive orthopaedic screw and the ability to deliver therapeutic agents to the surrounding tissue promotes successful tissue integration. Such local delivery of therapeutic agents can aid in such issues as improving the attachment strength of soft tissue to bone in reconstructive surgeries, improving the attachment strength of bone to screw, and strengthen bone in osteoarthritic or osteoporotic patients.

Another advantage is that the orthopaedic screw of the present invention can effectively be utilized for long term or short term delivery of therapeutic agents. Another advantage is that the therapeutic agent can be pre-loaded into the device at the factory or loaded by the surgeon before, during or after surgery.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

The present invention provides a device which can have a porous nature and which has the ability to deliver therapeutic agents. The porous nature of the device of the present invention and the ability of the device of the present invention to deliver therapeutic agents therethrough addresses existing deficiencies in the known art by promoting successful tissue integration.

The present invention provides a screw that is porous and/or can deliver therapeutic agents to the surrounding tissue. The materials to create this screw can be any implantable polymer, metal or ceramic or combinations of these. Possible polymers include PEEK (Poly(etheretherketone)), PEK (Poly(etherketone)), PAEK (poly(aryletherketone)), polyethylene, and resorbable polymers such as PLA (Poly(lactic acid)) and PGA (poly(glycolic acid)). Likely first candidates are PEEK, reinforced PEEK (reinforcing materials include but are not limited to carbon fiber/particles/nanotubes, barium sulfate, zirconia) and titanium/titanium alloys. The screw of the present invention can include, but does not need to include, the ability to deliver therapeutic agents (such as drugs or biologics) to the surrounding tissue. The therapeutic agent can be selected by the surgeon before the surgery, at the time of surgery, or at any point in time thereafter. In addition, the therapeutic agent can be pre-loaded into the device at the factory through currently acceptable practices or loaded by the surgeon before, during, or after surgery (as a follow-up procedure).

The screw of the present invention can be porous but does not need to be porous.

I. Porous Structure—Design Options According to the Present Invention

Figure 1:
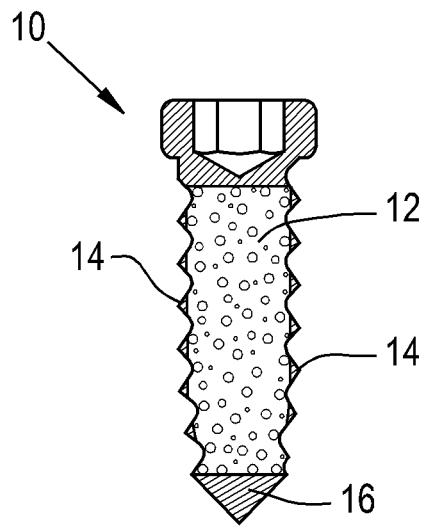
FIG. 1 is a section view of a porous screw with solid outer threads and tip according to the present invention.

Screw 10 of the present invention can be fully porous or have select regions of solid material. For example, screw 10 may include porous region 12 and a solid region of material at the outer portion of threads 14 and leading tip 16 of screw 10. The solid region of material at the outer portion of threads 14 and leading tip 16 of screw 10 may be desired due to the high stresses these regions can see during screw insertion (see FIG. 1). In addition, a very rough porous structure on the outer portion of the threads can cause insertion of the screw to be difficult due to its potential to grab versus slide past or cut through bone/soft tissue. In another example, the head (not shown) of screw 10 may be solid. This solid material can be formed of any implantable polymer, reinforced polymer, or metal.

Figure 2A:
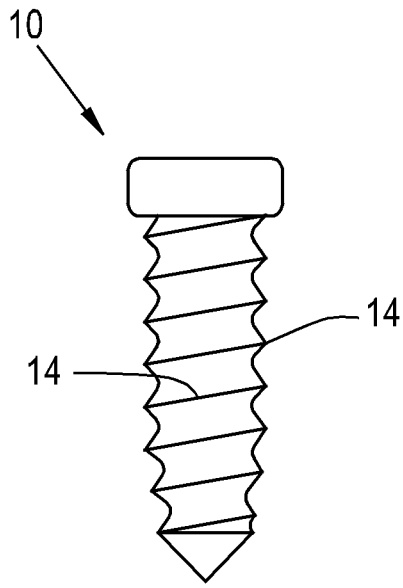
FIG. 2A shows a view of a screw having a continuous thread.
Figure 2B:
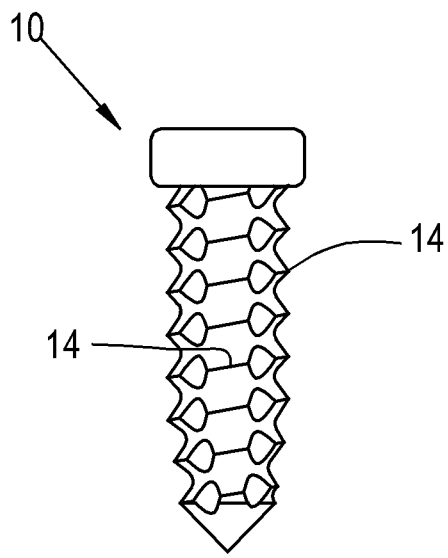
FIG. 2B shows a view of a screw having a discontinuous thread.

Thread 14 can be continuous (see FIG. 2A) or discontinuous (see FIG. 2B) and be a single or multiple lead thread.

The porosity of the screw can vary within the region(s), including changes in pore shape, size, and density. These characteristics can vary along the length of the screw axis and/or radially (from the outer diameter to the axis).

Delivery of Therapeutic Agents

Another way of improving integration of the surrounding tissue is to deliver therapeutic agents that promote positive tissue response (e.g. increased growth rate, decreased inflammatory response). The orthopaedic screw of the present invention can be used to locally deliver such therapeutic agents to the tissue surrounding the device. Such local delivery of therapeutic agents can aid in such issues as improving the attachment strength of soft tissue to bone in reconstructive surgeries, improving the attachment strength of bone to the screw, and strengthen bone in osteoarthritic or osteoporotic patients. Therapeutic agents include, but are not limited to, hydroxyapatite, drugs, and biologics.

Screws allowing for localized delivery of therapeutic agents, according to the present invention, can be, but need not be, porous. Porous screws according to the present invention can, but need not, allow for localized delivery of therapeutic agents.

Figure 3:
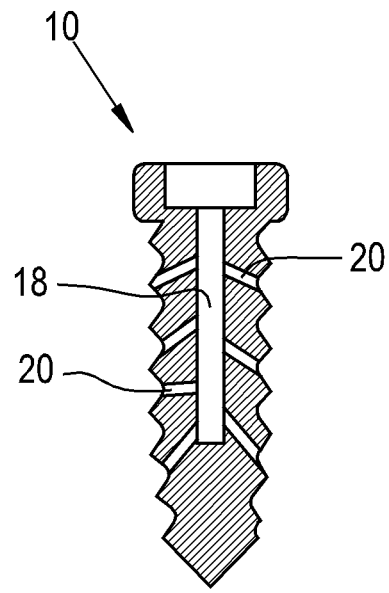
FIG. 3 illustrates an implant according to the present invention for immediate delivery of a therapeutic agent.
Figure 4:
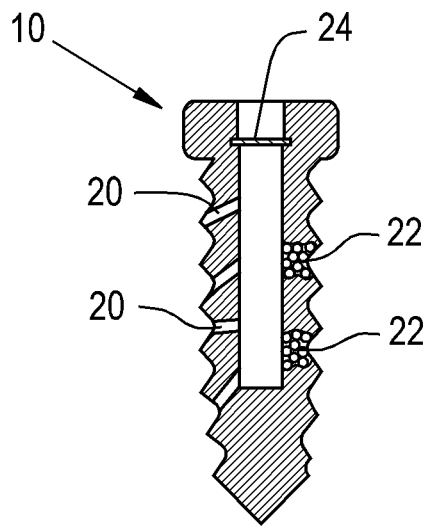
FIG. 4 illustrates an implant according to the present invention for immediate or sustained delivery of a therapeutic agent.
Figure 5:
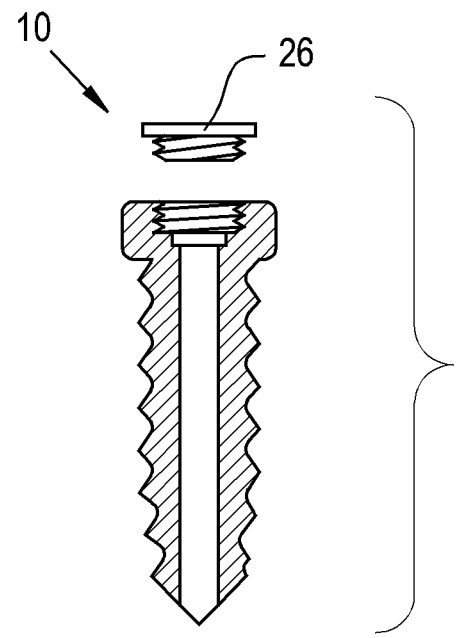
FIG. 5 illustrates a therapeutic agent delivery implant according to the present invention with sealing cap.
Figure 6:
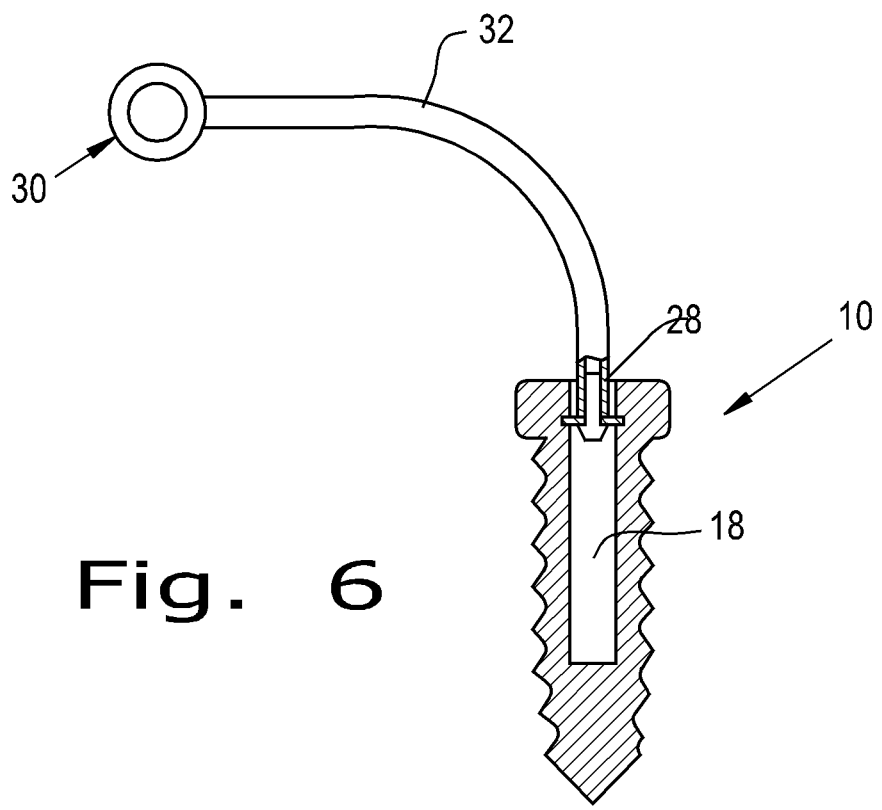
FIG. 6 illustrates an implant according to the present invention with port attachment features.

Screw 10 can contain reservoirs 18 for the long-term delivery of the therapeutic agents, as illustrated in FIG. 4 and/or channels/holes 20, as illustrated in FIG. 3, for immediate, local delivery of therapeutic agents. Screw 10 can further include a plurality of interconnected pores (22) allowing for local delivery of a therapeutic agent to the surrounding tissue, as shown in FIG. 4. These options are described as follows:

1. Long term delivery.
   a. Reservoirs. One or more reservoirs 18 can allow for the long term (hours to weeks) delivery of the therapeutic agents. Access to delivery channels 20, reservoir 18, etc. of screw 10 is gained by several ways including:
      i. Self-sealing polymer diaphragm 24 can allow for direct interface with a needle at the time of surgery or post-surgery (see FIG. 4).
      ii. A removable cap 26 made of PEEK or another implantable material can also provide access to the therapeutic agent delivery features and seal these features after delivery of the therapeutic agent (FIG. 5). A tool that facilitates insertion of the screw could also aide in assembling cap 26 to the screw.
   b. Connect to another device. Access to the therapeutic agent delivery features of the screw can be provided by interfacing screw 10 with a device designed to deliver therapeutic agents from subcutaneous to elsewhere in the body (e.g. a port that is frequently used to deliver therapeutic agents from sub-skin to a vein deeper in the chest cavity). The last option can include attachment feature 28 on screw 10 that directly interfaces with port 30, interfaces with catheter 32 (which interfaces with the port 30) or interfaces with an additional component, which can be attached to screw 10 to interface with port 30 or catheter 32—See FIG. 6).

2. Immediate delivery. No reservoir is required for this approach. The access means of the reservoir design above (self-healing polymer diaphragm 24 and removable cap 26) can also be used to access delivery channels 20 in this design. This design can also include a simple interface with a delivery tool. An example of this is a simple slip fit between a delivery needle and the screw's cannula.

A given screw can contain any or all of these options.

Cannulation

The screws can be cannulated or non-cannulated.

Radiopaque Markers—Polymer Implants

Figure 7A:
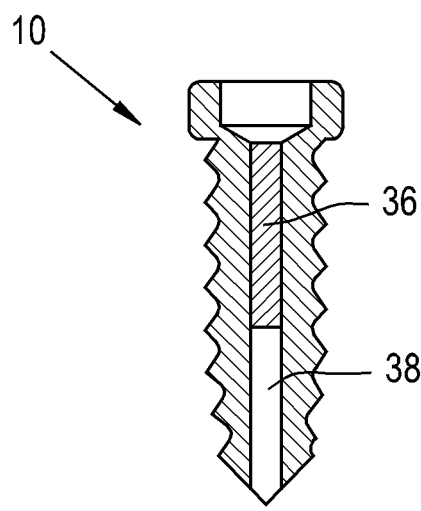
FIG. 7A illustrates an implant according to the present invention including a radiopaque marker.
Figure 7B:
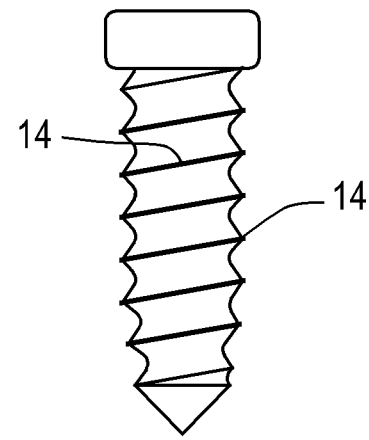
FIG. 7B illustrates an implant according to the present invention including a radiopaque marker.
Figure 7C:
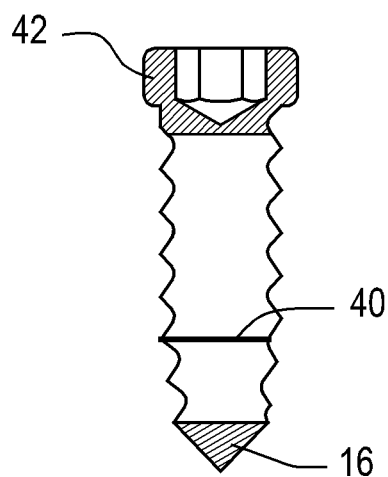
FIG. 7C illustrates an implant according to the present invention including a radiopaque marker.

If the implant according to the present invention is made of a radiolucent material (for example polymers such as PEEK), radiopaque markers 34 can be included to indicate position and orientation of the implant on an x-ray, fluoroscope, or similar diagnostic tool. Markers can be made of any number of more dense implantable materials. Options include, but are not limited to, implantable metals (stainless steel, titanium, or titanium alloys for example), barium sulfate filled PEEK, carbon filled PEEK, or other polymers with radiopaque material (such as barium sulfate or zirconium dioxide). Examples of the marker design include one or more of the following: pin 36 filling some or all of cannula 38 of a cannulated screw, one of the material layers if the manufacturing method involves material layering (discussed below), all or some of threads 14, cross pin 40, or head 42 or tip 16 of the screw (see FIGS. 7A-C). The opacity and/or amount of radiopaque material can be controlled so that the marker does not prevent evaluation of the tissue near the screw by x-ray or other diagnostic ways (as occurs with current solid metal screws).

II. Porous Structure—Manufacturing Options According to the Present Invention

The porous structure of the present invention can be manufactured using a variety of methods. These manufacturing options according to the present invention include seven options as follows:

1. Rolled. A porous sheet can be, for example, rolled into a screw. This is essentially the reverse of making a radial, spiral cut that is parallel to the axis of the screw. Layers of different materials can be combined in this process. This process involves the following:
   a. Make a porous sheet with holes in a pattern so that they line up when rolled.
   b. Roll sheet. This step can be performed with or without the aid of a center mandrel or rod.
      1. The sheet can be rolled without the aid of any center mandrels. This can create a cannulated screw. A biocompatible pin/rod can be inserted in any center hole and bonded to the screw to create a non-cannulated screw.
      2. The sheet can be rolled around a removable mandrel. This can create a cannulated screw. A biocompatible pin/rod can be inserted in any center hole and bonded to the screw to create a non-cannulated screw.
      3. Alternately the sheet can be rolled around and bonded to a biocompatible rod, creating a non-cannulated screw.
   c. Bond the rolled material.
2. Spiraled layers. This method is similar to the rolled approach, but this method involves bands of material that are wrapped around one another. The main difference between this method and that of rolling is that in this method, the bands of material translate along the axis while they are wrapped. Bands of several materials can be combined and intertwined. All bands can have the same direction and pitch of winding or different directions and pitches. These bands can be wrapped around a mandrel that is later removed to aid in bonding and to create a cannula. They can also be wrapped around a pin which they are then bonded to, creating a non-cannulated screw. An alternate option for creating a non-cannulated screw is to create the screw with or without the aid of a mandrel, then insert and bond a pin within the center hole of the screw.
3. Layered/stacked. Make a number of layers that are stacked and bonded to create the screw. These layers can be parallel to one another. The faces of the layers are perpendicular to the axis of the screw, parallel to it, or any other angle of orientation. To reduce secondary operations, alignment of one layer to another may be desirable. Alignment of layer to layer can be achieved by such ways as alignment fixtures that line up the center cannula (if the screw is cannulated) of each layer to one another (by way of a pin for example), fixtures or implant components/features that align pore or thread features to one another, or fixtures or implant components/features that align features on the outer diameter of each layer to one another. Features can also be created within a given layer to aid in alignment and/or assembly (such as grooves and mating protrusions).

Note: The holes in options 1-3 can be created by, for example, laser cutting, punching, etching, electrical discharge machining, plasma etching, electroforming, electron beam machining, water jet cutting, stamping, or machining. For polymer based materials, they can be created as the sheets are created by, for example, extruding, injection molding, or hot stamping.

4. Dissolvable Material.
   a. One method involves creating a mixture of powdered implantable material (e.g. PEEK) and a powder (e.g. salt) that is soluble in something in which the implantable material is not soluble (such as water, isopropyl alcohol for the PEEK example). The mixture is then heated to bond the implantable particles together. Pressure can also be applied to aid in the bonding of particle to particle. Heat can be created by convection or other ways (such as coating the powder with a material that absorbs a given range of energy waves—such as laser waves—and causes heating. (e.g. Clearweld coating by Gentex® Corporation)). Finally, dissolve away the filler to create the porous implantable material. This method can create net shape parts or raw material shapes from which individual parts can be created.
   b. Another method involves mixing an implantable polymer with a dissolvable material such as described above. The mixture is then pelletized and then injection molded to an intermediary or the final part shape. The filler is dissolved away to create the porous implantable polymer.

5. Stereolithography.
6. Laser or Electron Beam Sintering of Powdered Material.
7. A combination of the above methods: for example, using the dissolvable method to create microporous sheets of PEEK, then stamping larger pores and stacking to create a screw.

III. How to Bond Parts Containing Polymer(s)
Options for Bonding Processes
1. Heat. Heat can be generated in several ways:
   a. Ultrasonic welding—use ultrasonic waves to create heat at the interface of layers.
   b. Heat staking—use a heated tool to cause melting between the layers.
   c. Vibratory welding.
   d. Laser welding.
   e. Convection—use an oven to create heat to cause bonding.
   f. Intermediary layer—for example, use a material that can absorb energy waves that pass through the polymer (for example PEEK) without causing damage. The absorbed energy will cause localized heating. An example of such a coating is Clearweld by Gentex® Corporation. The laser waves that Clearweld absorbs pass through the PEEK without causing damage, allowing the layers to be melted together without large scale damage to the PEEK.
2. Chemical.
   a. Adhesives—a secondary material (such as adhesive) can be used to bond the material.
   b. Solvent bonding—a material in which the polymer or reinforced polymer is soluble can be applied to the sheet surfaces allowing multiple surfaces to be bonded to one another.
   c. Overmolding—overmolding of the polymer or reinforced polymer can provide a chemical bonding
3. Mechanical.
   a. Overmolding—overmolding of a polymer or reinforced polymer can create a mechanical lock between components on a micro or macro scale (microscale—the molded material locks with surface asperities of the existing material. Macroscale—features such as tongue-groove connections or undercuts). The overmolded material can be a separate component from the layers or one layer can be overmolded onto another layer.
   b. Features are provided within the layers or by a separate component which provides a mechanical lock—e.g. a pin, snap lock connection, dove-tail, tongue-groove, rivet, melting tabs to create a mechanical lock, etc.
   c. Some adhesives provide a mechanical bond in addition to or instead of a chemical bond.
4. Combinations of Any/All of the Above Methods.
Order of Processes
1. Bond all layers together at once—especially attractive for methods utilizing energy waves to trigger bonding (e.g. Clearweld coating by Gentex® Corporation or ultraviolet light curable adhesives).
2. Simultaneously bond and roll/stack layers at once—again, may be especially attractive for methods utilizing energy waves to trigger bonding (e.g. if light cannot penetrate all layers of a rolled design in order to activate an adhesive, the rolling operation could take place in a light box allowing for a continuous rolling and adhesive curing operation.
3. Roll/stack layers and bond in increments. This could add a single layer at a time or multiple layers.

IV. How to Bond Metal/Metal Alloy Parts
Options for Bonding Processes
1. Heat.
   a. Laser welding—layers can be laser welded in a number of locations. Two or more layers or wraps of material can be welded together at once depending on the size of the part and alignment of the pores (the laser can access several layers to be bonded through the porosity).
   b. Spot welding—traditional spot welding can be used to bond two or more layers/wraps of material.
   c. Diffusion bonding/sintering.
   d. Vibratory welding.
   e. Ultrasonic welding.
2. Adhesives.
3. Mechanical ways. Features are provided within the layers or by a separate component which provides a mechanical lock—e.g. a pin, snap lock connection, dove-tail, tongue-groove, rivet, melting tabs to create a mechanical lock etc.
4. Overmolding with an implantable polymer. Overmolding of PEEK or another implantable polymer can create a mechanical lock between components on a micro or macro scale (microscale—the molded material locks with surface asperities of the existing material. Macroscale—features such as tongue-groove connections or undercuts). The overmolded material can be a separate component from the layers or one layer can be overmolded onto another layer.
Order of Processes
As with the polymer materials discussed above, two or more layers of metal can be bonded during increments or as a continuous stacking/bonding process.

V. Making Threads—Manufacturing Options According to the Present Invention
1. Form the threads after the layers have been bonded to create a screw blank (see FIG. 13)
   a. Machine the threads
   b. Hot form the threads with a mold
2. Form threads in the sheets prior to bonding.
   a. Rolling method: The material will not actually create the complete thread shape until the sheets are formed into the final shape. Continuous or discontinuous threads can be created. Design options for this method include creating raised material that forms the threads or removing material to leave the thread material. The raised material in the first method can be created by way of machining, laser ablation, hot stamping, hot or cold forming, chemical etching, electro-discharge machining and similar methods. The material of the second method can be removed by way of machining, laser cutting, stamping, etching, punching, electro-discharge machining, water jet cutting, electron beam machining or other means.
   b. Stacking method: Continuous or discontinuous threads can also be created by this method. The 'ears' of material in each layer form the threads when the layers are stacked. These can be created by way of machining, hot stamping, hot or cold forming, dies/punches, chemical etching, electro-discharge machining and similar methods.
3. Add separate threads—Threads can be formed separately and attached to the screw blank. The material for these threads can include: biocompatible polymers, reinforced biocompatible polymers and/or biocompatible metals. The attachment ways for these threads include:

a. Mechanical attachment—press/interference fit, tabs.
b. Overmolding—mold the solid, porous, or reinforced polymer screw inside of the solid threads or mold the porous, solid or reinforced polymer threads onto the already formed screw.
c. Adhesive or solvent bonding.

VI. Cannulation—Manufacturing Options According to the Present Invention

With any of the manufacturing methods, screws can be created with or without a cannula.
1. Cannulated.
   a. Rolling method. In this method, it can be desirable to wind the material around a mandrel that is at the center of the screw, running along its axis. This mandrel can be removed to leave an open cannula.
   b. Layered method. A center hole at the axis of each layer is created to form the cannula when they are stacked together.
2. Non-cannulated.
   a. Rolled method.
      i. The sheet can also be bonded to the mandrel, with the mandrel forming a portion of the implant. This mandrel can be solid or porous and of any implantable material such as PEEK or titanium.
      ii. In addition, the material can be formed around a removable mandrel, creating a cannula. This cannula can be then be filled with a biocompatible material that is attached/bonded to the screw.
   b. Layered method. The layers that are stacked to create the screw can have solid material in place of the holes that would create the cannula. Alternately, they can have cut-outs creating the cannula and this cannula can be filled with a biocompatible material that is attached/bonded to the screw.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic device comprising:
   a therapeutic agent; and
   a screw having a reservoir and a plurality of porous bands in fluid connection with said reservoir and extending from said reservoir to an outside surface of the screw, said plurality of porous bands being separated by at least one non-porous region of the screw, said screw configured to deliver said therapeutic agent from said reservoir through said plurality of porous bands to a surrounding tissue when said screw is implanted in said tissue.

2. The orthopaedic device of claim 1, wherein said therapeutic agent is one of hydroxyapetite, drugs and biologics.

3. The orthopaedic device of claim 1, further comprising a self-sealing diaphragm configured for injection of said therapeutic agent into said screw.

4. The orthopaedic device of claim 1, further comprising a removable self-sealing cap configured for sealing said screw after delivery of said therapeutic agent.

5. The orthopaedic device of claim 1, further comprising a port and a catheter, wherein said screw is configured to receive said therapeutic agent through said port.

6. The orthopaedic device of claim 1, wherein said screw is cannulated.

7. The orthopaedic device of claim 1, wherein said plurality of porous band include at least one first set of said plurality of interconnected pores and at least one second set of said plurality of interconnected pores, said at least one first set of said plurality of interconnected pores and said at least one second set of said plurality of interconnected pores being configured to deliver said therapeutic agent from said screw to said surrounding tissue.

8. The orthopaedic device according to claim 1, wherein said screw is non-cannulated.

* * * * *